US012797426B2

(12) United States Patent
Parker et al.

(10) Patent No.: US 12,797,426 B2
(45) Date of Patent: Nov. 17, 2026

(54) CANNABINOID CONCENTRATION PROCESS

(71) Applicant: PPM Labs LLC, Anacortes, WA (US)

(72) Inventors: Ray Okada Parker, Everett, WA (US); John Sant Parker, Everett, WA (US); Douglas Montague Pratt, Anacortes, WA (US); Mark Christian Miller, Pateros, WA (US)

(73) Assignee: PPM Labs LLC

( * ) Notice: Subject to any disclaimer, the term of this patent is extended or adjusted under 35 U.S.C. 154(b) by 0 days.

(21) Appl. No.: 17/318,600

(22) Filed: May 12, 2021

(65) Prior Publication Data

US 2022/0362319 A1 Nov. 17, 2022

(51) Int. Cl.
*A61K 36/185* (2006.01)
*A61K 31/00* (2006.01)

(52) U.S. Cl.
CPC ........ *A61K 36/3482* (2024.05); *A61K 31/658* (2023.05); *A61K 2236/31* (2013.01); *A61K 2236/51* (2013.01); *A61K 2236/55* (2013.01)

(58) Field of Classification Search
None
See application file for complete search history.

(56) References Cited

U.S. PATENT DOCUMENTS

2020/0101041 A1* 4/2020 Kleidon ................. A61K 31/05
2020/0138072 A1* 5/2020 Yucel ...................... A23P 10/30

FOREIGN PATENT DOCUMENTS

CN 106995958 * 8/2017
WO WO 2020/176806 * 3/2020
WO WO 2020/176896 * 9/2020

OTHER PUBLICATIONS

Total filtration, 7 pages, 2023.*
Dictionary.com, Kief, https://www.dictionary.com/browse/kief, 2025.*
Dictionary.com, Inflorescence, https://www.dictionary.com/browse/inflorescence, 2025.*

* cited by examiner

*Primary Examiner* — Michael V Meller
(74) *Attorney, Agent, or Firm* — AEON Law, PLLC; Adam L.K. Philipp; Charlotte E. Holoubek

(57) ABSTRACT

The present application discloses a process for the purification and concentration of cannabinoids from *cannabis* inflorescence. Kief, or resinous trichomes, are suspended in water in order to be treated by electrolysis. The mixture is then filtered by an electrically charged depth filter. The mixture is then concentrated via a Tangential Flow Filter. The resulting concentrate may be at least one of THC, THCa, CBD, CBG, CBDV, CBDA, THCV, CBCA, THCVA, CBDVA, and CBCVA.

14 Claims, 1 Drawing Sheet

CANNABINOID CONCENTRATION PROCESS

TECHNICAL FIELD

The present application relates to the separation and concentration of cannabinoids from *cannabis* inflorescence. More specifically, the present application relates to mechanical separation, dissolution, electrolysis, and filtration of *Cannabis* inflorescence to produce concentrated cannabinoids or acidic cannabinoids.

BACKGROUND

*Cannabis* has been used medicinally for many years, and in Victorian times was a widely used component of prescription medicines. It was used as a hypnotic sedative for the treatment of "hysteria, delirium, epilepsy, nervous insomnia, migraine, pain and dysmenorrhea." Historically, *cannabis* was regarded by many physicians as unique; having the ability to counteract pain resistant to opioid analgesics, in conditions such as spinal cord injury, and other forms of neuropathic pain including pain and spasm in multiple sclerosis.

The use of *cannabis* continued until the middle of the twentieth century, when the recreational use of *cannabis* prompted legislation which resulted in the prohibition of its use. The utility of *cannabis* as a prescription medicine is now being re-evaluated. The discovery of specific cannabinoid receptors and new methods of administration have made it possible to extend the use of *cannabis*-based medicines to historic and novel indications.

The principle cannabinoid components present in herbal *cannabis* are the cannabinoid acids Δ9-tetrahydrocannabinolic acid (Δ9-THCA) and cannabidiolic acid (CBDA), with small amounts of the corresponding neutral cannabinoids, respectively Δ9-tetrahydrocannabinol (Δ9-THC) and cannabidiol (CBD). Cannabidiol was formerly regarded as an inactive constituent, however there is emerging evidence that it has pharmacological activity, which is different from that of Δ9-THC in several respects.

Purified forms of certain of the cannabinoids present in herbal *cannabis* are useful as active pharmaceutical agents. For example, Δ9-THC (also known as dronabinol) has been approved by the Food and Drug Administration (FDA) for the control of nausea and vomiting associated with chemotherapy, and also shows potential pharmacological activity in the treatment of glaucoma, migraine headaches, anxiety, and as an analgesic. Cannabidiol, formerly regarded as an inactive constituent of *cannabis*, has, as aforesaid, itself shown promising pharmacological activity.

Thus, there remains a need for purified forms of cannabinoid acids and cannabinoids present in *cannabis* herb, including the major cannabinoids Δ9-THC and CBD.

SUMMARY OF THE INVENTION

The present application discloses a process for the purification and concentration of cannabinoids from *cannabis* inflorescence. Kief, or resinous trichomes, may first be removed from the flower. The kief may then be ground up, dissolved in water and strained. The mixture may then again be suspended in water and prefiltered at 10 μm under vacuum. The mixture may then again be resuspended in water in order to be treated by electrolysis. The mixture may then again be prefiltered at 10 μm under vacuum. The mixture may then be filtered by a 3M Zeta Filter product.

The mixture may then be concentrated via a Tangential Flow Filter. The resulting product may be concentrated THCa and CBD.

DETAILED DESCRIPTION

Figure 1:
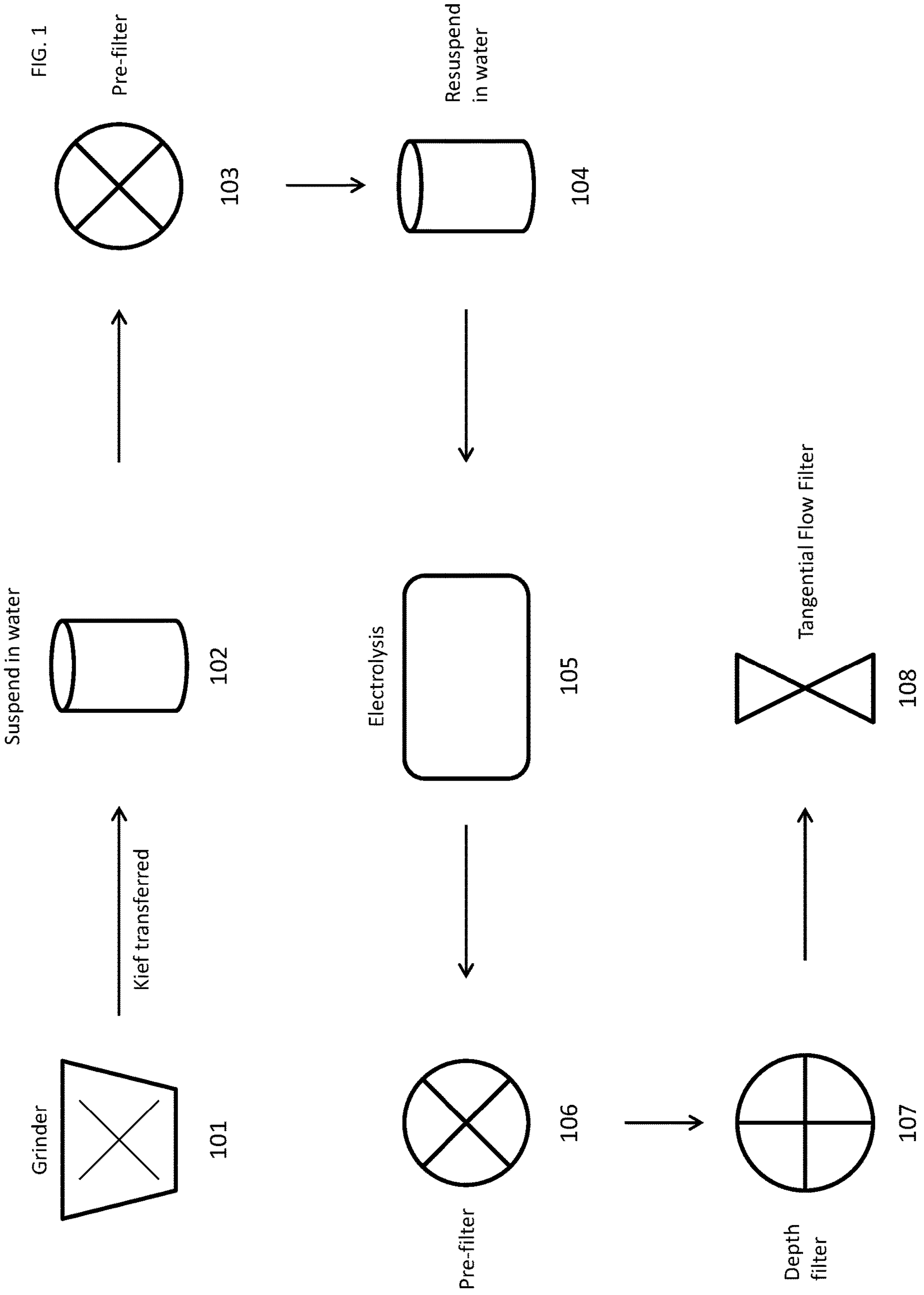
FIG. 1 is a flow chart of the Novel Cannabinoid Purification Process.

In the Summary above and in this Detailed Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range including that number (which may be a range having an upper limit or no upper limit, depending on the variable being defined). For example, "at least 1" means 1 or more than 1. The term "at most" followed by a number is used herein to denote the end of a range, including that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)–(a second number)," this means a range whose limits include both numbers. For example, "25 to 100" means a range whose lower limit is 25 and upper limit is 100, and includes both 25 and 100.

The present application discloses process for the purification and concentration of THCa and CBD from *cannabis* inflorescence. Trichome separation has traditionally been done using methods such as supercritical $CO_2$ extraction or ethanol separation. These processes, however, involve large, capital-intensive equipment and use undesirable chemicals. The present application discloses a process which uses no alcohols/solvents (aside from testing the resulting products) for separation and purification, is more natural than supercritical $CO_2$ extraction, or hydroxyl/alcohol based-soaking/separation methods currently on the market today. The present process uses electricity as a means of separation instead of other types of separation. The present process uses commercial off-the-shelf materials in novel way around separation of cannabinoid matter. The present process is much cheaper than traditional supercritical extraction and other industry-standard processes. The present process is more efficient in terms of time and resources, higher product yield than industry standards, less waste created than industry standards. An overall diagram and detailed diagram are listed in FIG. 1.

To start, the kief may be removed from inflorescence by grinding, shown on FIG. 1 as 101. Large pieces of plant material may be removed and rerun through process. 3 grams of kief may be collected for separation and suspended in 250 mL of distilled or regular water. The mixture may be stirred until homogeneous using a heat exchanger and more agitation/mixing, 102, in order to optimize the process, but the boiling point for most major chemicals of interest is 157-180° C. so temperature should be kept below this value. pH, salt concentrations, reagent concentrations, kief concentrations, and other polymer-based extracts may all be added or modified in the future for optimization. In one embodiment, the initial pH is 6.7, the salt concentration is 100 ppm, the kief concentration is 1.2 g/L and there are no added reagents or polymer-based extracts.

The mixture may then be pre-filtered, 103, with 10 μm 7 s/100 mL/in filter paper to remove small impurities and low molecular weight species. Using vacuum filtration at 3-4 psi, agitation and heat exchanger may optimize the process.

The pre-filter material may be resuspended by scraping off the supernatant from the filter using mechanical device. This material may contain the cannabinoid matter of interest. The material may then be resuspended in 10 mL of distilled or regular water, 104. The suspension may be mixed well to ensure all matter is removed from the pre-filter.

The suspension may then be placed into a container to begin the electrolysis process, 105. Two bars of aluminum may act as cathode and anode. A 30 A constant current power supply set at 30 volts and 2 amps may be used. The mixture may be constantly stirred and agitated during the process. pH, salt concentrations, reagent concentrations, kief concentrations, and other polymer-based extractants may be modified in the future for optimization. Electrolysis may proceed 12 hours. Foam and other particulates may form during the process. Electrolysis may be stopped when a desired concentration of cannabinoids is achieved.

The electrolysis mixture may then be pre-filtered, 106, with 10 μm 7 s/100 mL/in filter paper to remove small impurities and low molecular weight species. Using vacuum filtration at 3-4 psi, agitation and heat exchanger may optimize the process.

The eluate may then be retained. Pre-filter may be discarded. The eluate material may be modified in the future by varying pH, salt concentrations, reagent concentrations, kief concentrations, and other polymer-based extractants for better results.

The eluate may then be processed through a 3M Zeta Plus BC Series Capsule, EXT Series with SP Filter Media, 60SP03 A Grade. 3-4 psi of vacuum may be applied. The eluate material may be pumped through the depth filter, shown on FIG. 1 as 107, to finalize separation process. The eluate from the charged depth filter may then be retained.

The depth filter eluate may be concentrated using a Millipore Minitan Tangential Flow Cassette, 108, to remove water, other impurities, and other reagents used in purification.

The final concentrate of one embodiment comprises THC, THCa, CBD. Other embodiments of the invention may result in concentrates comprising CBG, CBDV, CBDA, THCV, CBCA, THCVA, CBDVA, and/or CBCVA.

Below, three actual sets of results from an embodiment of the invention are shown in a table. The table demonstrates the effectiveness of the invention. A Baseline test measured the cannabinoid content of each Trial before electrolysis. After electrolysis and filtering, the filtered content of each Trial was reduced, indicating that the filtrate contained increased cannabinoid content, shown as the Final FIGURES.

| | Trial 1 | Trial 2 | Trial 3 |
|---|---|---|---|
| Kief Weight (grams) | 3.003 g | 3.006 g | 3.009 g |
| Volts/Amps | 30 v/2 amps | 30 v/2 amps | 30 v/2 amps |
| Runtime | 4 hours | 12 hours | 12 hours |
| Volume Distilled Water | 250 ml | 250 ml | 250 ml |
| Baseline: Before Electrolysis | | | |
| Cannabinoid content | 18.05% | 12.43% | 20.60% |
| Final: After Electrolysis | | | |
| Cannabinoid content | 12.10% | 9.27% | 11.73% |
| % Extracted from Electrolysis | 32.96% | 25.42% | 43.06% |

Thus, it can be determined that the procedure, including electrolysis, increases yields over previous methods.

The invention claimed is:

1. A process for the concentration of at least one cannabinoid from raw plant material using electrolysis, an electrically charged depth filter, and a tangential flow filter, wherein the process is performed without alcohols/solvents for separation and purification.

2. The process of claim 1, wherein the concentrate comprises at least one of THC, THCa, and CBD.

3. The process of claim 1, wherein the concentrate comprises at least one of CBG, CBDV, CBDA, THCV, CBCA, THCVA, CBDVA, and CBCVA.

4. A process for the concentration of at least one cannabinoid from raw plant material using electrolysis, an electrically charged depth filter, and a tangential flow filter, wherein the raw plant material comprises *cannabis* inflorescence, comprising:

removing kief from *cannabis* inflorescence;

suspending the kief in water to form a first suspension;

prefiltering the first suspension using a filter having an effective pore size of substantially 10 μm under vacuum to obtain retained material;

resuspending the retained material in water to form a second suspension and subjecting the second suspension to electrolysis to form an electrolysis mixture;

prefiltering the electrolysis mixture using a filter having an effective pore size of substantially 10 μm under vacuum and retaining an eluate;

filtering the eluate using the electrically charged depth filter; and concentrating an eluate from the electrically charged depth filter using the tangential flow filter.

5. The process of claim 4, wherein the electrolysis is performed using two aluminum electrodes.

6. The process of claim 4, wherein the electrolysis is performed at about 30 volts and about 2 amps.

7. The process of claim 4, wherein the process is performed without alcohols/solvents for separation and purification.

8. The process of claim 4, wherein the electrically charged depth filter comprises a 3M Zeta Plus BC Series Capsule, EXT Series with SP Filter Media, 60SPO3 A Grade.

9. The process of claim 4, wherein the tangential flow filter comprises a Millipore Minitan tangential flow cassette.

10. The process of claim 4, wherein the prefiltering is performed at a vacuum measuring substantially between 3-4 psi.

11. The process of claim 4, wherein the concentrate comprises at least one of THC, THCa, and CBD.

12. The process of claim 4, wherein the concentrate comprises at least one of CBG, CBDV, CBDA, THCV, CBCA, THCVA, CBDVA, and CBCVA.

13. A process for the concentration of at least one cannabinoid from raw plant material using electrolysis, an electrically charged depth filter, and a tangential flow filter, wherein the raw plant material comprises *cannabis* inflorescence, comprising:

removing kief from *cannabis* inflorescence;

suspending the kief in water to form a first suspension;

prefiltering the first suspension under vacuum to obtain retained material;

resuspending the retained material in water to form a second suspension and subjecting the second suspension to electrolysis to form an electrolysis mixture;

prefiltering the electrolysis mixture under vacuum and retaining an eluate;

filtering the eluate using the electrically charged depth filter; and concentrating an eluate from the electrically charged depth filter using the tangential flow filter;

wherein the process is performed without alcohols/solvents for separation and purification.

14. The process of claim 13, wherein the concentrate comprises at least one of THC, THCa, and CBD.

* * * * *